United States Patent [19]

Strege

[11] 4,341,905

[45] Jul. 27, 1982

[54] INORGANIC HALIDE SALT CATALYSTS FOR HYDROXYALKYLATION OF PHENOLS OR THIOPHENOLS

[75] Inventor: Paul E. Strege, Midland, Mich.

[73] Assignee: The Dow Chemical Company, Midland, Mich.

[21] Appl. No.: 179,129

[22] Filed: Aug. 18, 1980

Related U.S. Application Data

[63] Continuation-in-part of Ser. No. 58,705, Jul. 18, 1979, abandoned.

[51] Int. Cl.³ .......................................... C07C 41/16
[52] U.S. Cl. .................................... 568/45; 568/27; 568/48; 568/49; 568/55; 568/644; 568/648; 568/649; 568/656; 568/642; 568/584; 568/640; 568/608; 546/134
[58] Field of Search .................. 568/648, 608, 55, 27, 568/48, 49, 45, 644, 649, 656, 642, 584, 640; 546/134

[56] References Cited

U.S. PATENT DOCUMENTS

| | | | |
|---|---|---|---|
| 2,075,018 | 3/1937 | Bruson et al. | 568/648 |
| 2,448,767 | 9/1948 | Carlson | 568/648 X |
| 3,354,227 | 11/1967 | Katzschmann | 568/648 X |

OTHER PUBLICATIONS

Levin et al., Chem. Abs., vol. 59, (1965), 7338(d).
Yoshino et al., Bull. Chem. Soc. Japan 47 (1973), 553–556.
Shapiro et al., J. of Chem., USSR5, (1968), 200–203.

*Primary Examiner*—Bernard Helfin
*Attorney, Agent, or Firm*—Douglas N. Deline

[57] ABSTRACT

Hydroxyalkylphenyl ether or thioether compounds are prepared by reaction of cyclic organic carbonate compounds with phenols or thiophenols in the presence of an alkali metal halide catalyst.

9 Claims, No Drawings

INORGANIC HALIDE SALT CATALYSTS FOR HYDROXYALKYLATION OF PHENOLS OR THIOPHENOLS

CROSS-REFERENCE TO RELATED APPLICATION

This is a continuation-in-part of parent application Ser. No. 058,705, filed July 18, 1979 and now abandoned.

BACKGROUND OF THE INVENTION

The present invention relates to a process for the preparation of hydroxyalkylphenyl ether or thioether compounds. More particularly, the present invention is concerned with improved catalysts for use in the preparation of compounds by the reaction of cyclic organic carbonate compounds with phenols and thiophenols.

Carlson disclosed in U.S. Pat. No. 2,448,767 a method of hydroxyethylation wherein ethylene carbonate or ethylene sulfite was reacted with certain organic compounds including phenols and alcohols. The reaction could be carried out in the presence or in the absence of a suitable solvent, and in the presence or in the absence of a suitable catalyst. Catalysts that were disclosed included an acid (concentrated sulfuric acid or an alkyl ester of sulfuric acid), a base (alkali carbonates), or the alkali salt of a phenol. The preferred catalyst was an alkali carbonate or alkali salt of a phenol. U.S. Pat. No. 3,283,030 disclosed use of potassium carbonate as a basic catalyst in the reaction of ethylene carbonate with certain substituted phenols.

Alkali metal hydrides disclosed by U.S. Pat. No. 2,987,555 and alkali metal hydroxides disclosed by U.S. Pat. No. 2,967,892 have also been found to be effective catalysts for hydroxyalkylation reactions of ethylene carbonate with phenols and chloromethylethylene carbonate with phenols respectively.

One disadvantage associated with prior art processes using acidic or basic catalysts has been the occurrence of secondary reactions between the hydroxyalkylphenyl ether product and the carbonate reactant forming quantities of undesirable side-products. A further disadvantage of known prior art processes is the inability to use certain modified phenolic or thiophenolic compounds that are unstable under acidic or basic reaction conditions.

SUMMARY OF THE INVENTION

This invention comprises an improved process for the hydroxyalkylation of phenols or thiophenols providing high yields with good selectivity. In particular the invention comprises the use of certain alkali metal halide salts as reaction catalysts for the reaction of phenols or thiophenols and cyclic organic carbonate compounds. The ability to operate at a neutral pH according to the invention allows the reaction to be run under relatively mild conditions thereby allowing utilization of reactants having a greater variety of functionality than has been possible under prior known methods. It is also possible utilizing the invented process to attain reaction conditions conducive to exclusive monohydroxyalkylation of the phenol or thiophenol reactant. The hydroxyalkylphenyl ether or thioether products formed according to this invention are used as solvents and in certain coatings as well as in additional industrial applications.

DETAILED DESCRIPTION OF THE INVENTION

This invention lies in the discovery that certain alkali metal halide salts act as effective catalysts in the reaction of cyclic organic carbonate compounds with phenols or thiophenols.

The particular compounds useful as catalysts according to this invention include: the monofluoride salts of potassium, rubidium, and cesium; the monochloride salts of lithium, sodium, potassium, rubidium, and cesium; and the monobromide salts of lithium, sodium and potassium. The preferred catalysts for use according to this invention are the monochloride salts of lithium, sodium, potassium, rubidium and cesium, and the monofluoride salts of cesium, potassium, and rubidium. Most preferred catalysts are the monofluoride salts of cesium, potassium and rubidium.

The amount of alkali metal halide salt catalyst required to effectively catalyze the hydroxyalkylation reaction according to the present invention may vary compared to total reactant weight from about 0.1 percent to about 10.0 percent depending on the particular catalyst. It is preferred to employ the catalyst in amounts from about 0.5 percent to about 2.0 percent by weight. The weight ratios of those halide salts that form hydrates, e.g., $KF.2H_2O$, refer to the dehydrated halide salt weight.

The catalyst of this invention may be used by themselves or in combination with other known hydroxyalkylation catalysts. The catalysts may also be employed in an unsupported state or supported by attachment to inert supportive means such as particles of alumina, silica gel, diatomaecous earths, porous glasses, zeolites, and the like. By the term zeolites is included modern synthetic resin zeolites useful as ion-exchangers as well as the well-known naturally occurring mineral formations that may be used with or without modification as ion-exchangers. Attachment of the catalysts to such materials is known, one such method described in more detail in the following examples, having been disclosed by J. H. Clark in J.C.S. Chem. Comm., 789 (1978).

The phenol- or thiophenol-containing compounds that may be hydroxyalkylated by organic carbonate compounds according to this invention are extremely varied. Carlson in U.S. Pat. No. 2,448,767 discloses a wide variety of reactive hydrogen-containing aromatic compounds including phenol, thiophenol, alkaline salts of phenol, $\beta$-naphthol, and 8-hydroxyquinoline that are capable of undergoing hydroxyalkylation with alkyl carbonate compounds. Additionally Carlson taught that all such compounds tested responded to the hydroxyalkylation reaction and it was believed all such compounds would be responsive.

Davis in U.S. Pat. No. 2,987,555 discloses an additional number of phenols that may be hydroxyalkylated by reaction with alkylene carbonates including: p,p'-biphenol, p,p'-sec-butylidene diphenol, 4,4'-isopropylidenebis(o-cresol), 4,4'-isopropylidenebis(2-phenylphenol), o-chlorophenol, o-cresol, p-propylphenol, p-bis(o-cresol) and the like.

I have found that nearly any phenol- or thiophenol-containing reactant is suitable for use according to this invention. Included are: phenol, thiophenol and phenol or thiophenol compounds substituted with one or more hydroxy, mercapto, alkyl, aryl, alkaryl, aralkyl, halo or sulfonyl substituents, or mixtures thereof.

However, Tsuruya disclosed in *J. Polymer Sci.*, Part B, 7, 709 (1969) that 2,4,6-tribromophenol, preferably forms polymers through debromination when reacted with organic carbonate compounds. This compound therefore is not considered to be suitable for use according to the present invention.

The cyclic organic carbonates used in the hydroxyalkylation reactions according to this invention may likewise be varied. In addition to ethylene carbonate, Davis in U.S. Pat. No. 2,987,555 disclosed that any cyclic alkylene carbonate having the appropriate carbonate moiety attached at adjacent positions was capable of undergoing hydroxyalkylation with phenolic compounds. Specifically mentioned carbonate compounds were propylene carbonate, 1,2- or 2,3-butylene carbonate and phenylethylene carbonate. For said disclosure I do incorporate this teaching by reference.

In addition, ethers of alkylene carbonates of the formula

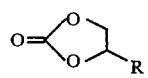

wherein R is $C_{1-20}$ alkoxy, alkoxyalkylene, or (poly)alkoxyalkylene may be used.

As previously mentioned, use of the alkali metal halide salts as catalysts at a neutral pH in the practice of this invention instead of acidic or basic catalysts advantageously permits the use of reactants containing greater functionality. The catalysts and milder reaction conditions additionally allow greater selectivity in product formation including the exclusive formation of the monohydroxyalkylated product without concomitant formation of secondary reaction products.

The reaction may take place in the presence or absence of an inert solvent. In the preferred embodiment the cyclic carbonate reactant is a suitable solvent.

The reactants may be combined in nearly any molar ratio since some product is produced under nearly all conditions. It is preferred however, to combine the reactants in a stoichiometric ratio thereby eliminating the need to remove excess reactants from the finished product in a subsequent purification step.

The reaction may be carried out in any vessel suitably designed to contain the reactants and products and be unreactive under the conditions of the invention. Representative of suitable reaction vessels are those made of glass, stainless steel or other unreactive material.

The reaction may be run in the practice of this invention at any suitable temperature from about 100° C. to about 210° C. Faster reaction rates are observed at higher temperatures but decomposition of reactants and products is likely to occur at the higher temperatures. The optimum temperature for particular reactants allowing fast reaction rates, but minimizing decomposition side-products may be easily determined according to ordinary techniques of experimentation. The preferred operating temperature for most phenolic and carbonate reactants is from about 150° C. to about 170° C. Heating the reaction vessel to the operating temperature may conveniently be occasioned by any usual means such as a heat lamp, heating mantle, oil bath, etc.

The time for the reaction to proceed to substantial completion will vary depending on various factors such as the particular phenol- or thiophenol-containing reactant, cyclic organic carbonate reactant, the catalyst and temperature selected. Generally about two hours to about five hours is sufficient. The evolution of carbon dioxide is a convenient indicator of the progress of the reaction.

The reaction may be run either accompanied by mechanical or magnetic stirring or without stirring. To avoid liquid entrapment during the evolution of carbon dioxide it is also advantageous to employ a condenser according to well-known techniques in the art.

The product, a corresponding hydroxyalkyl ether or thioether derivative may be easily recovered from the reaction mixture, for example, by distillation if a liquid, or by recrystallization if a solid.

While the invention has been described as useful in a batch process reaction, it may be utilized equally advantageously in a continuous reaction process.

SPECIFIC EMBODIMENTS OF THE INVENTION

Having described the invention the following examples are given merely as illustrative of the present invention and are not to be considered as limiting.

EXAMPLE 1

Ethylene carbonate (89.9 g, 1.02 mole), phenol (94.1 g, 1.0 mole) and potassium fluoride (1 g, 0.5 percent of total reactant weight) were placed in a 500 ml round-bottomed flask equipped with a condenser and gas bubbler. A magnetic stirrer provided agitation. The mixture was heated to 160° C.±2° C. in an oil bath. After 2.5 hours the reaction vessel was removed from the oil bath, cooled and the contents removed. Purification of the product by distillation gave 137 g of 2-phenoxyethanol (99 percent conversion based on phenol limiting reagent).

EXAMPLES 2–13

The reaction conditions of Example 1 were repeated using a variety of halide salts as catalysts. All catalysts were present in a 2 weight percent concentration based on the combined weight of phenol and ethylene carbonate. The reaction temperature was maintained between about 160° C. and about 165° C. Table I shows the reaction time and indicated extent of reaction. Some results in Table I are the average of more than one run.

TABLE I

| Example | Catalyst | Reaction Time (hours) | % Completion |
|---|---|---|---|
| 2 | CsF | 1.5–2 | 98 |
| 3 | KF | 1.75–2.25 | 98 |
| 4 | RbF | 3 | 95 |
| 5 | NaCl | 3 | 94 |
| 6 | RbCl | 4 | 94 |
| 7 | KCl | 4.25 | 94 |
| 8 | CsCl | 4 | 92 |
| 9 | LiCl | 5 | 94 |
| 10 | NaBr | 7 | 93 |
| 11 | KBr | 4.25 | 78 |
| 12 | LiBr | 7 | 74 |
| 13 | No Catalyst | >6.0 | <20 |

EXAMPLE 14

The reaction apparatus used in Example 1 was charged with 4-methylphenol (54 grams), ethylene carbonate (45 grams) and a small amount of KF (0.5 grams, 0.5 percent). After thorough mixing the flask was immersed in an oil bath and the temperature adjusted to 160° C.±2°. After a reaction time of 1.1 hours, $CO_2$ evolution ceased and the product, 4-(2-hydroxyethoxy)-methylbenzene (71 grams, 94 percent yield) was recovered and purified by recrystallization from acetone.

EXAMPLES 15-29

The reaction conditions of Example 14 were repeated using phenol reactants more specifically identified in Table II below. The catalyst was KF present in the indicated weight percent. The product in Examples 15–29 in each case was the corresponding 2-hydroxyethyl ether derivative of the initial phenol reactant.

TABLE II

| Example | Phenol | Amount (g) | Ethylene Carbonate wt. (g) | Catalyst % | Time (hrs) | Yield % |
| --- | --- | --- | --- | --- | --- | --- |
| 15 | 2-methylphenol | 54 | 45 | 0.5 | 2.0 | 91 |
| 16 | 1-methylphenol | 54 | 45 | 0.5 | 1.5 | 87 |
| 17 | 4-methoxyphenol | 62 | 45 | 0.5 | 1.8 | 92 |
| 18 | 4-chlorophenol | 64 | 45 | 0.5 | 1.5 | 95 |
| 19 | 3-chlorophenol | 64 | 45 | 0.5 | 3.5 | 90 |
| 20 | 2-chlorophenol | 64 | 45 | 0.5 | 1.0 | 92 |
| 21 | 4-nitrophenol | 70 | 45 | 0.4 | 15 | 71 |
| 22 | 3-nitrophenol | 59 | 38 | 0.5 | 8 | 79 |
| 23 | 2-nitrophenol | 70 | 45 | 0.4 | 8 | 86 |
| 24 | 2,4,6-trimethylphenol | 45 | 30 | 0.4 | 3.3 | 78 |
| 25 | 4-tert-butylphenol | 75 | 45 | 0.4 | 3 | 92 |
| 26 | 4-phenylphenol | 85 | 45 | 0.4 | 2.7 | 97 |
| 27 | 2-phenylphenol | 85 | 45 | 0.4 | 1.5 | 95 |
| 28 | 2,2'-thiobis(4-phenylphenol) | 10 | 4.9 | 0.9 | 72 | 80 |
| 29 | 4-bromophenol | 86 | 44 | 0.4 | 3.5 | 93 |

EXAMPLES 30-33

Supported potassium fluoride catalysts were prepared by combining as an aqueous slurry potassium fluoride and the supportive material described in more detail below. Excess water was then removed by evaporation to yield the desired supported catalyst.

| Example | Support | Wt. % KF |
| --- | --- | --- |
| 30 | silica gel | 12.5 |
| 31 | silica gel | 11.1 |
| 32 | alumina | 11.1 |
| 33 | *zeolite | 11.1 |

*The zeolite used a strongly basic, macroporous, styrene-divinylbenzene copolymeric resin in the MSA-1 ion-exchange form sold commercially as Dowex MSA-1 ion-exchange resin.

EXAMPLE 34

Ethylene carbonate (44.0 g, 0.5 mole), phenol (47.1 g, 0.5 mole) and 4.5 g of the supported catalyst prepared in Example 30 consisting of 0.56 g KF catalyst were combined in a 250 ml round-bottom flask equipped with a condenser and gas bubbler. Agitation was provided by a magnetic stirrer. The reaction was conducted in an oil bath maintained at 160° C.±2°. After 2 hours heating was discontinued and the product remaining in the flask was allowed to cool. Filtration to remove the catalyst gave 69.0 g (100 percent yield) of a slightly yellow liquid shown by vapor phase chromatography and infrared spectroscopy to be phenoxyethanol of 98 percent purity.

EXAMPLE 35-38

The reaction conditions of Example 34 were repeated using the supported and unsupported catalysts more fully described in the following chart. Approximate reaction times required to produce 95 percent yield are taken as an indication of the effectiveness of the supported catalyst.

| Example | Catalyst | Approx. time to produce 95% yield (min.) |
| --- | --- | --- |
|  | unsupported |  |
| 35 | $KF.2H_2O$ (0.5 g) | 58 |
| 36 | Example 31 (4.5 g) | 72 |
| 37 | Example 32 (4.5 g) | 105 |
| 38 | Example 33 (4.5 g) | 60 |

EXAMPLES 39-42

Phenol was combined with the following ethers of alkylene carbonates and KF catalyst in a 25 ml round-bottomed flask. The flask was then placed in an oil bath maintained at 160° C.±2° C. After the specified time the identified product was recovered in the yield indicated. All amounts are by weight.

| Example | % Catalyst | Time (hr) | Carbonate | Product | Yield (%) |
| --- | --- | --- | --- | --- | --- |
| 39 | 0.54 | 1 | ethylene carbonate | $\phi\text{-}OC_2H_5OH$ | 98 |
| 40 | 0.28 | 20 | ![cyclic carbonate with CH2OCH(CH3)2] | $\phi\text{-}OCH_2CH(OH)CH_2OCH(CH_3)_2$ | 86 |
| 41 | 1.29 | 16 | ![cyclic carbonate with CH2OC(CH3)3] | $\phi\text{-}OCH_2CH(OH)CH_2OC(CH_3)_3$ | 84 |

-continued

| Example | % Catalyst | Time (hr) | Carbonate | Product | Yield (%) |
|---|---|---|---|---|---|
| 42 | 0.67 | 6 | (4-membered cyclic carbonate with CH₂O—φ substituent) | φ-OCH₂CH(OH)CH₂O—φ | 86 |

φ = phenyl

EXAMPLES 43–50

The reaction conditions of Examples 39–42 were repeated using KF catalyst and thiophenol and 4-methylthiophenol reactants.

| Example | % Catalyst | Time (hr) | Thiophenol Reactant | Carbonate | Product | % Yield |
|---|---|---|---|---|---|---|
| 43 | 1.11 | 0.5 | φSH | ethylene carbonate | φ-SC₂H₄OH | 84 |
| 44 | 0.82 | 0.25 | " | cyclic carbonate with CH₂OCH(CH₃)₂ | φ-SCH₂CH(OH)CH₂OCH(CH₃)₂ | 96 |
| 45 | 0.77 | 0.33 | " | cyclic carbonate with CH₂OC(CH₃)₃ | φ-SCH₂CH(OH)CH₂OC(CH₃)₃ | 95 |
| 46 | 0.72 | 18 | " | cyclic carbonate with CH₂Oφ | φ-SCH₂CH(OH)CH₂Oφ | 70 |
| 47 | 1.16 | 15 | 4-methyl-thiophenol | ethylene carbonate | p-tolyl-SCH₂CH₂OH | 90 |
| 48 | 0.88 | 15 | 4-methyl-thiophenol | cyclic carbonate with CH₂OCH(CH₃)₂ | p-tolyl-SCH₂CH(OH)CH₂OCH(CH₃)₂ | 99 |
| 49 | 0.83 | 15 | 4-methyl-thiophenol | cyclic carbonate with CH₂OC(CH₃)₃ | p-tolyl-SCH₂CH(OH)CH₂O(CH₃)₃ | 94 |
| 50 | 0.78 | 15 | 4-methyl-thiophenol | cyclic carbonate with CH₂—O—φ | p-tolyl-SCH₂CH(OH)CH₂O—φ | 95 |

φ = phenyl

What is claimed is:

1. In the method of hydroxyalkylation wherein phenol- or thiophenol-containing compounds are reacted with cyclic organic carbonate compounds in the presence of a catalyst followed by recovery of the hydroxyalkylaryl ether or thioether formed, the improvement wherein the reaction is conducted without addition of strong acid or base and the catalyst is an inorganic halide salt selected from a group consisting of potassium fluoride, rubidium fluoride, cesium fluoride, lithium chloride, sodium chloride, potassium chloride, rubidium chloride, cesium chloride, lithium bromide, sodium bromide and potassium bromide.

2. The process of claim 1 wherein the phenol- or thiophenol-containing compound and organic carbonate compound are combined in substantially stoichiometric quantity.

3. The process of claim 1 wherein the carbonate compound is ethylene carbonate.

4. The process of claim 1 wherein the reaction is carried out at a temperature from about 100° C. to about 210° C.

5. The process of claim 1 wherein the quantity of catalyst present based on total reactant weight is from about 0.1 to about 10 weight percent.

6. The process of claim 1 wherein the catalyst is selected from a group consisting of potassium fluoride, rubidium fluoride, cesium fluoride, lithium chloride, sodium chloride, potassium chloride, rubidium chloride and cesium chloride.

7. The process of claim 1 wherein the catalyst is selected from a group consisting of potassium fluoride, rubidium fluoride and cesium fluoride.

8. The process of claim 1 wherein the catalyst is attached to an inert supportive means.

9. The process of claim 8 wherein the inert supportive means are particles of alumina, silica gel, diatomaceous earths, porous glasses or zeolites.

* * * * *

UNITED STATES PATENT AND TRADEMARK OFFICE
CERTIFICATE OF CORRECTION

PATENT NO. : 4,341,905

DATED : July 27, 1982

INVENTOR(S) : Paul E. Strege

It is certified that error appears in the above—identified patent and that said Letters Patent is hereby corrected as shown below:

Column 2, line 34, "diatomaecous" should read -- diatomaceous --.

Column 6, line 9, "used a" should read -- used was a --.

Column 6, line 10, "in the MSA-1 ion-exchange form" should read -- in the chloride form --.

Signed and Sealed this

Eighteenth Day of January 1983

[SEAL]

Attest:

Attesting Officer

GERALD J. MOSSINGHOFF

Commissioner of Patents and Trademarks